(12) United States Patent
L'hote-Gaston et al.

(10) Patent No.: US 8,992,987 B2
(45) Date of Patent: Mar. 31, 2015

(54) POLYSACCHARIDE DERIVATIVES AND DOSAGE FORMS

(75) Inventors: Jennifer L'hote-Gaston, Midland, MI (US); Nicholas S. Grasman, Midland, MI (US); Jorg Theuerkauf, Lake Jackson, TX (US); Sjoerd A. De Vries, Terneuzen (NL)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/009,435

(22) PCT Filed: Mar. 29, 2012

(86) PCT No.: PCT/US2012/031106
§ 371 (c)(1),
(2), (4) Date: Oct. 2, 2013

(87) PCT Pub. No.: WO2012/138529
PCT Pub. Date: Oct. 11, 2012

(65) Prior Publication Data
US 2014/0017326 A1 Jan. 16, 2014

Related U.S. Application Data (60) Provisional application No. 61/472,224, filed on Apr. 6, 2011.

(51) Int. Cl.
*A61K 47/36* (2006.01)
*A61K 9/20* (2006.01)

(52) U.S. Cl.
CPC ............... *A61K 47/36* (2013.01); *A61K 9/2054* (2013.01); *A61K 9/2095* (2013.01)
USPC ............ 424/493; 424/489; 428/402; 264/109

(58) Field of Classification Search
None
See application file for complete search history.

(56) References Cited

U.S. PATENT DOCUMENTS

| | | | |
|---|---|---|---|
| 4,113,187 A | 9/1978 | Hoppen et al. |
| 4,159,345 A | 6/1979 | Takeo et al. |
| 4,734,285 A | 3/1988 | Alderman |
| 4,979,681 A | 12/1990 | Donges et al. |
| 5,478,578 A | 12/1995 | Arnold et al. |
| 5,488,104 A | 1/1996 | Eickemeyer |
| 5,725,884 A | 3/1998 | Sherwood et al. |
| 7,629,331 B2 | 12/2009 | Pipkin et al. |
| 2005/0008706 A1 | 1/2005 | Holm et al. |
| 2010/0151038 A1 | 6/2010 | Cabelka et al. |
| 2012/0029091 A1 | 2/2012 | Goerlach-Doht et al. |
| 2012/0164184 A1 | 6/2012 | Pipkin et al. |
| 2012/0232167 A1* | 9/2012 | Takeuchi et al. ............... 514/781 |
| 2013/0112787 A1 | 5/2013 | Pierini |

FOREIGN PATENT DOCUMENTS

| | | |
|---|---|---|
| EP | 0370447 | 5/1990 |
| EP | 0201895 | 4/1991 |
| EP | 0824107 | 4/1998 |
| EP | 0933079 | 8/1999 |
| EP | 0954536 | 11/1999 |
| EP | 1127895 | 8/2001 |
| EP | 1127910 | 8/2001 |
| GB | 804306 | 11/1958 |
| GB | 2262527 | 6/1993 |
| WO | 9311746 | 6/1993 |
| WO | 9600748 | 1/1996 |
| WO | 9831710 | 7/1998 |
| WO | 2007050075 | 5/2007 |
| WO | 2005104712 | 6/2007 |
| WO | 2008127794 | 10/2008 |
| WO | 2009015880 | 2/2009 |
| WO | 2008127794 | 6/2009 |
| WO | 2010106555 | 9/2010 |
| WO | 2012138529 A1 | 10/2012 |

OTHER PUBLICATIONS

Yu, Prediction of Bulk Powder Flow Performance Using Comprehensive Particle Size and Particle Shape Distributions J. Pharma, Sc. 2011, vol. 100, 284-293.
Witt, Direct Imaging of Very Fast Particles Opens the Applications of the Powerful (Dry) Dispersion for Size and Shape Characterization, Partec, 2004.
Witt, Current Limits of Particle Size and Shape Analysis with High Speed Image Analysis, Partec, 2007.

* cited by examiner

*Primary Examiner* — Robert A Wax
*Assistant Examiner* — Danah Al-Awadi (57) ABSTRACT

Polysaccharide derivatives having a median Equivalent Projected Circle Diameter (EQPC) of less than 140 micrometers and a particle size and shape distribution meeting condition A or B or both are useful for preparing dosage forms, particularly for preparing compressed sustained-release dosage forms: A. non-compacted polysaccharide derivative particles have a flowability of at least 45 g/sec through a vertically inverted cone having a vertex angle of about 40 and an outlet diameter of about 50 mm, or B. i) no more than 40 volume percent of the polysaccharide derivative particles are fine particles having a particle length LEFI of less than 40 micrometers and ii) no more than 40 volume percent of the polysaccharide derivative particles are fibrous particles, and the sum of the fine particles and the fibrous particles does not exceed 50 volume percent.

16 Claims, 3 Drawing Sheets

POLYSACCHARIDE DERIVATIVES AND DOSAGE FORMS

CROSS REFERENCE TO RELATED APPLICATIONS

This application is a 35 USC §371 national phase filing of PCT/US2012/031106, filed 29 Mar. 2012, which claims the benefit of Application No. 61/472,224, filed Apr. 6, 2011.

FIELD

This invention relates to novel polysaccharide derivatives and dosage forms produced from one or more polysaccharide derivatives, one or more active ingredients, and one or more optional adjuvants.

BACKGROUND

Sustained release dosage forms have found wide usage in a variety of technology areas, such as in personal care or agricultural applications, water treatment and particularly in pharmaceutical applications. Sustained release dosage forms are designed to release a finite quantity of a compound into an aqueous environment over an extended period of time. Known sustained release pharmaceutical dosage forms contain a medicament or a vitamin whose rate of release is controlled by a polymeric matrix. Sustained release pharmaceutical dosage forms are desirable because they provide a method of delivering a long-lasting dose in a single application without overdosing. U.S. Pat. No. 4,734,285 discloses that the release of an active composition from a solid tablet can be prolonged by employing a fine particle sized hydroxypropyl methylcellulose ether composition as an excipient in the solid tablet. The particle size of the hydroxypropyl methylcellulose ether is so small that at least 90 percent by weight of the cellulose ether particles pass through a 100 mesh screen (149 micrometers mesh size), and preferably at least 97 percent by weight of the cellulose ether particles pass through a 140 mesh screen (105 micrometers mesh size) to achieve a long release profile. While such hydroxypropyl methylcellulose ether particles provide excellent release profiles to tablets, these particles of very small size are known to have poor flow properties. A poor flowability of the cellulose ether particles can lead to problems in the manufacturing of dosage forms such as tablets. Problems can include increased variability in tablet weight or tablet crushing strength from tablet-to-tablet as well as variation in the amount of active ingredient incorporated into each dosage form. Poor particle flow can also lead to consolidation of the powder bed in processing equipment, such as storage bins and tablet press feed hoppers.

The International Patent Application Publication No. WO 2008/127794 addresses the poor flowability of the hydroxypropyl methylcellulose ether disclosed in U.S. Pat. No. 4,734,285. WO 2008/127794 discloses a granular material having a mean particle diameter of 150 to 800 micrometers and an untapped bulk density of 0.1 to 0.35 g/cm$^3$, the main component of the granular material being a cellulose derivative. The granular material is a useful excipient for sustained-release dosage forms, particularly for excipients to be used in a direct compression process, due to the good flow and the good compactibility of the granular material leading to strong, hard tablets, with small variability in tablet-to-tablet physical properties, in combination with reproducible kinetics of the sustained release of the active ingredient. Unfortunately, it has been found that the low density of the granular material may cause some problems when blending the granular material with the active ingredient. Due to the low density of the granular material, the weight of the blend of granular material and active material in the blender typically has to be reduced to avoid overfilling of the blender, which reduces the throughput through the blender. Also, formulators may need to pre-compress the blend of granular material and active ingredient to be able to fill tablet dies with the target tablet weight.

Accordingly, one object of the present invention is to find polysaccharide derivatives which are useful as an excipient in dosage forms, particularly as excipients in sustained release dosage forms, and which have an improved flowability, as compared to the cellulose ethers disclosed in U.S. Pat. No. 4,734,285. Another object of the present invention is to find polysaccharide derivatives which are useful as an excipient in dosage forms, particularly as excipients in sustained release dosage forms, and which have an improved flowability and/or an increased bulk density, as compared to the cellulose ethers disclosed in WO 2008/127794.

SUMMARY

One aspect of the present invention is a polysaccharide derivative having a median Equivalent Projected Circle Diameter (EQPC) of less than 140 micrometers and a particle size and shape distribution meeting condition A or B or both:

A. non-compacted polysaccharide derivative particles have a flowability of at least 45 g/sec through a vertically inverted cone having a vertex angle of about 40° and an outlet diameter of about 50 mm, or B. i) no more than 40 volume percent of the polysaccharide derivative particles are fine particles having a particle length, LEFI, of less than 40 micrometers and ii) no more than 40 volume percent of the polysaccharide derivative particles are fibrous particles, and the sum of the fine particles and the fibrous particles does not exceed 50 volume percent.

Another aspect of the present invention is a dosage form which has been produced from a) one or more of the above-mentioned polysaccharide derivatives, one or more active ingredients, and one or more optional adjuvants.

Yet another aspect of the present invention is a process for preparing a dosage form which comprises the step of I.) blending one or more of the above-mentioned polysaccharide derivatives, one or more active ingredients, and one or more optional adjuvants, and II.) compressing the blend to a dosage form.

Yet another aspect of the present invention is the use of an above-mentioned polysaccharide derivative for producing a dosage form.

DETAILED DESCRIPTION

The polysaccharide derivatives of the present invention have a median Equivalent Projected Circle Diameter (EQPC)

of less than 140 micrometers. EQPC of a particle is defined as the diameter of a circle that has the same area as the projection area of the particle. The EQPC of particles can be determined using a high speed image analysis method which combines particle size and shape analysis of sample images. Such method is described in more details further below and in the prior art cited further below. A high speed image analysis system is commercially available from Sympatec GmbH, Clausthal-Zellerfeld, Germany as dynamic image analysis (DIA) system QICPIC™. For the purpose of the present invention the median EQPC is the volume distribution average of all particles in a given sample of a particulate polysaccharide derivative. The median EQPC means that 50% of the EQPC of the particle distribution is smaller than the given value in μm and 50% is larger. Polysaccharide derivatives which are useful in the present invention have a median EQPC of less than 140 micrometers, preferably of no more than 130 micrometers, more preferably of no more than 125 micrometers and most preferably of no more than 120 micrometers. Polysaccharide derivatives which are useful in the dosage form of the present invention generally have a median EQPC of at least 30 micrometers, preferably at least 35 micrometers, more preferably at least 40 micrometers, and most preferably at least 45 micrometers. WO 2008/127794 discloses a granular material having a mean particle diameter of at least 150 micrometers, using a RapidVue 5× image analyzer which is commercially available from Beckman Coulter, Inc., California. USA; this corresponds to a median EQPC of at least 141 micrometers, measured using the dynamic image analysis (DIA) system QICPIC™.

It has been surprisingly found that the flowability of polysaccharide derivatives, particularly cellulose derivatives, in particulate form does not only depend on the median EQPC but also on the percentage of fine particles and fibrous particles. A polysaccharide derivative in particulate form, particularly a cellulose derivative, generally contains particles of regular and irregular shapes. It has been surprisingly found that the flowability of a polysaccharide derivative can be controlled, influenced, and/or varied by classifying the particles of the polysaccharide derivative into fine particles of a certain maximum length as described further below, fibrous particles of a certain shape as described further below, and other particles and by controlling, influencing and/or varying the relative volume proportions of the fine particles, fibrous particles and other particles. For the purpose of the present invention, the "other particles", i.e., the particles which do not meet the definition of "fine particles" and "fibrous particles" are designated as "spherical particles". It has also been found that the relative volume proportion of the fine particles, fibrous particles and other particles does not only have an impact on the flow-ability of the polysaccharide derivative, but generally also on the bulk density of the polysaccharide derivative. When the polysaccharide derivative is used for producing dosage forms, such as tablets, it has even more surprisingly been found that the relative volume proportions of the fine particles, fibrous particles and other particles has an impact on the tablet to tablet variability of tablet weight and tablet hardness. A low tablet to tablet variability of tablet weight and tablet hardness is highly desirable.

The volume proportions of the fine particles, fibrous particles and other particles of the polysaccharide derivative can be determined by a high speed image analysis method which combines particle size and shape analysis of sample images. An image analysis method for complex powders is described in: W. Witt, U. Köhler, J. List, Current Limits of Particle Size and Shape Analysis with High Speed Image Analysis, PARTEC 2007. A high speed image analysis system is commercially available from Sympatec GmbH, Clausthal-Zellerfeld, Germany as dynamic image analysis (DIA) system QICPIC™. The high speed image analysis system is useful for measuring the following dimensional parameters of particles:

LEFI: The particle length LEFI is defined as the longest direct path that connects the ends of the particle within the contour of the particle. "Direct" means without loops or branches.

DIFI: The projection area of the particle divided by the sum of all lengths of the branches of the particle.

Elongation: The particle elongation is the ratio of the diameter DIFI and the length LEFI of a particle, as defined by the formula DIFI/LEFI.

EQPC: EQPC of a particle is defined as the diameter of a circle that has the same area as the projection area of the particle.

Feret Diameter: Feret Diameter is also known as the caliper diameter. The distance between two tangents on opposite sides of a particle profile, that are parallel to some fixed direction, is the Feret Diameter. If a particle has an irregular shape, the Feret diameter usually varies much more than with regularly shaped particles.

Minimal Feret Diameter (Fmin): The minimum distance between pairs of tangents to the particle projection in some fixed direction. The minimal Feret diameter is the smallest diameter after consideration of all possible orientations (from 0° to 180°). For irregularly shaped particle, Fmin can be significantly smaller than EQPC.

Maximal Feret Diameter (Fmax): The maximum distance between pairs of tangents to the particle projection in some fixed direction. The maximal Feret diameter is the largest diameter after consideration of all possible orientations (from 0° to 180°). Fmax can be significantly larger than EQPC.

Aspect ratio: The aspect ratio of a particle in the powder is the ratio of minimal to the maximal Feret diameter, Fmin/Fmax, and is another measure for the particle shape. Fmin/Fmax is between 0 and 1 for any particle.

Sphericity: The ratio of the perimeter of a circle that has the same area as the projection area of the particle, PEQPC, to the perimeter of the real particle. Since the equivalent circle gives the smallest possible perimeter at a given projection area, the value of sphericity is between 0 and 1 for any particle. The smaller the value, the more irregular the shape of the particle.

Use of a Dynamic Image Analysis DIA system QICPIC™ equipped with a RODOS dry powder disperser from Sympatec GmbH, Clausthal-Zellerfeld, Germany for a variety of powders is described in: W. Yu, K. Muteki, L. Zhang, and G. Kim, Prediction of Bulk Powder Flow Performance Using Comprehensive Particle Size and Particle Shape Distributions, JOURNAL OF PHARMACEUTICAL SCIENCES, VOL. 100, NO. 1, JANUARY 2011.

The volume of each particle type (fine particles, spherical particles and fibrous particles) in the powder sample is calculated from the medians of the number distribution of the respective LEFI and DIFI for fibrous particles, and the respective EQPC for fine particles and spherical particles. Number distributions are calculated from the DIFI, EQPC and LEFI for each particle within the sample.

Fine Particles:

For the purpose of the present invention fine particles have a particle length LEFI of less than 40 micrometers and generally a particle length LEFI of at least 10 micrometers. The detection limit of the QICPIC™ with a M7 optical system is 10 micrometers.

The volume of the fine particles in a sample of a polysaccharide derivative can be calculated according to Equation 1

$$V = \frac{\pi (EQPC)^3}{6} n,  \quad\text{(Equation 1)}$$

wherein V is the volume of fine particles, n is the number of fine particles in the sample and EQPC here is the median EQPC determined from the number particle size distribution of the fine particles.

Fibrous Particles and Spherical Particles

For the purpose of the present invention a distinction between fibrous particles and other (spherical) particles is made if the particles have a particle length LEFI of more than or equal to 40 micrometers. This distinction is made based on the parameters from the image analysis that describes the shape of the particles; these parameters are elongation, sphericity and aspect ratio as defined above.

Fibrous Particles

Fibrous particles, as generally understood by the skilled artisan, are typically particles characterized by irregular shape and length typically much larger than the diameter. Fibers can be straight or curved, thin or thick. Consequently, both shape and size information from the QICPIC™ is used to define the fibrous particles. For the purpose of the present invention particles are "fibrous" particles if they meet one of the following definitions I or II: I) particles with an elongation equal or less than 0.35, an aspect ratio of equal or less than 0.45, and a LEFI of equal or greater than 40 micrometers; or II) particles with an elongation equal or less than 0.35, an aspect ratio of greater than 0.45, a sphericity of less than 0.7 and a LEFI of equal or greater than 40 micrometers.

The volume of fibrous particles in a sample of a polysaccharide derivative can be calculated according to Equation 2

$$Vf = \frac{\pi}{4} (DIFI)^2 LEFI \, n_f, \quad\text{(Equation 2)}$$

wherein $V_f$ is the volume of fibrous particles, $n_f$ is the number of fibrous particles in the sample, DIFI is the median projection area of the particles divided by the sum of all lengths of the branches of the particles determined from the number particle size distribution of the fibrous particles and LEFI is the median particle length determined from the number particle size distribution of the fibrous particles.

Spherical Particles

For the purpose of the present invention particles meet the definition of "spherical particles" if they have an elongation equal or less than 0.35, and an aspect ratio greater than 0.45, and a sphericity equal or greater than 0.70, and a LEFI equal or greater than 40 micrometers. For the purpose of the present invention particles also meet the definition of "spherical particles" if they have an elongation greater than 0.35 and a LEFI equal or greater than 40 micrometers.

The volume of the spherical particles in a sample of a polysaccharide derivative can be calculated according to Equation 3

$$Vs = \frac{\pi (EQPC)^3}{6} n_s, \quad\text{(Equation 3)}$$

wherein Vs is the volume of spherical particles, $n_S$ is the number of spherical particles in the sample and EQPC here is the median EQPC determined from the number particle size distribution of the spherical particles. Alternatively, the volume of the spherical particles can be calculated by subtracting the volume of the fine particles and the volume of the fibrous particles from the total volume of the sample.

The volume fractions can be readily calculated from the volumes V, Vs and Vf as defined above. Since the densities of an individual fine particle, of an individual fibrous particle and of an individual spherical particle are all essentially the same, the volume fractions essentially correspond to the weight fractions.

In one aspect the polysaccharide derivatives of the present invention have a volume fraction of fine particles of no more than 40%, preferably no more than 35%, more preferably no more than 30% and most preferably no more than 28%. Polysaccharide derivatives of the present invention generally have a volume fraction of fine particles of at least 2%. Moreover, polysaccharide derivatives of the present invention have a volume fraction of fibrous particles of no more than 40%, preferably no more than 30% and more preferably no more than 20%. Typically the polysaccharide derivatives of the present invention have a volume fraction of fibrous particles of one percent or more. It has been found that the volume fraction of fibrous particles in the polysaccharide derivatives of the present invention is smaller than the volume fraction of fibrous particles in known polysaccharide derivatives. Moreover, the sum of the fine particles and of the fibrous particles in the polysaccharide derivatives of the present invention is not more than 50 volume percent, preferably not more than 45 volume percent, more preferably not more than 40 volume percent, most preferably not more than 35 volume percent, and particularly not more than 30 volume percent. Accordingly, polysaccharide derivatives of the present invention have a volume fraction of non-fine and non-fibrous other (i.e., spherical) particles of at least 50%, preferably at least 55%, more preferably at least 60%, most preferably at least 65%, and particularly at least 70%.

Bulk density as used herein is defined as the ratio of apparent mass to volume of a material taken, called untapped bulk density. A useful procedure for measuring the untapped bulk density is described in the example section. Polysaccharide derivatives which are useful in the present invention generally have an untapped bulk density of more than 150 kg/m$^3$, preferably more than 300 kg/m$^3$, more preferably more than 350 kg/m$^3$, and most preferably 400 kg/m$^3$ or more.

Figure 1:
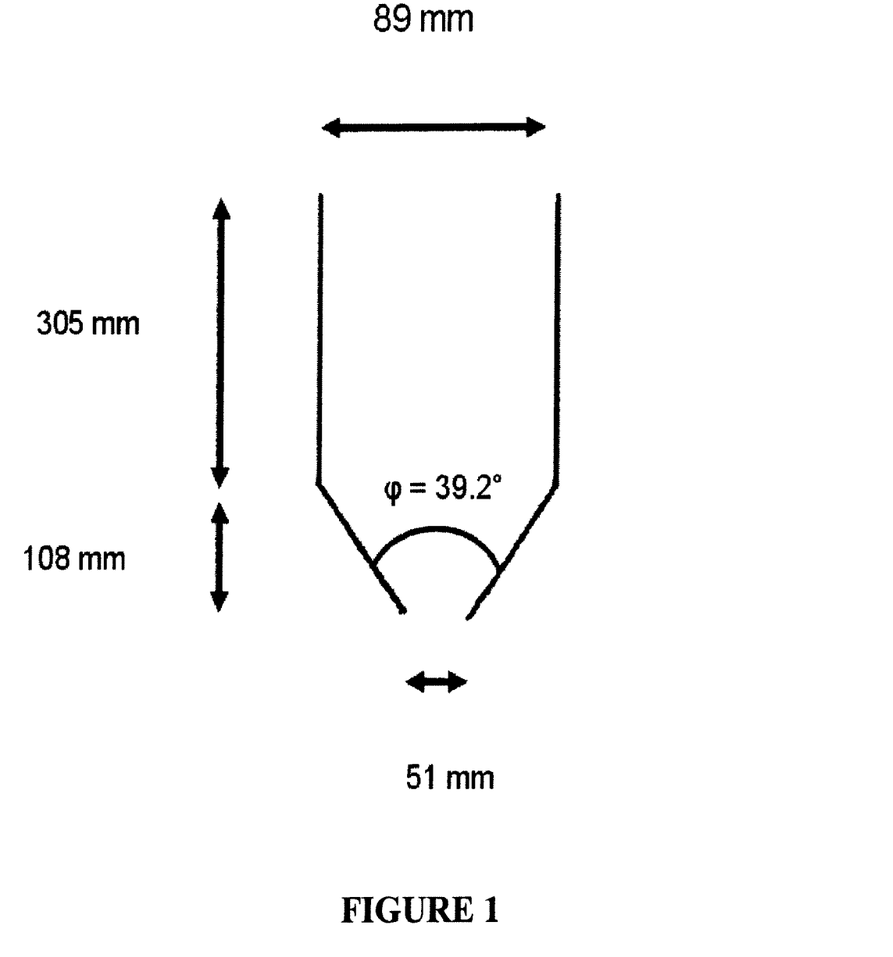
FIG. 1 represents a schematic illustration of an apparatus for testing the flowability of a polysaccharide derivative in particulate form.

In another aspect the polysaccharide derivatives of the present invention have a flowability of at least 45 g/sec, preferably at least 50 g/sec, and more preferably at least 60 g/sec. Their flowability generally is up to 90 g/sec, but in ideal cases the flowability can be up to 100 g/sec or even up to 120 g/sec. The flowability as used herein is defined as the amount of the polysaccharide derivative particles that flows out of a flow test apparatus having a vertically arranged column of about 300 mm with a diameter of about 90 mm and a conic shaped bottom geometry having a height of about 110 mm, a vertex angle of about 40° and an outlet diameter of about 50 mm. The flow test apparatus is described in more detail in the examples and is illustrated in FIG. 1. Surprisingly the polysaccharide derivatives of the invention have particle flow that exceeds polysaccharide derivatives known in the art with an equivalent bulk density.

The polysaccharide derivatives of the present invention preferably have a median LEFI of from 60 to 350 micrometers, more preferably from 63 to 300 micrometers, most preferably from 65 to 270 micrometers. The median LEFI means that 50% of the LEFI of the particle distribution is smaller than the given value in μm and 50% is larger, as calculated from the volume distribution.

Preferred polysaccharide derivatives are polysaccharide ethers and polysaccharide esters, more preferably cellulose derivatives, such as cellulose ethers and esters, most preferably water-soluble cellulose ethers. They can have one or more substituents, preferably of the types: hydroxyethyl, hydroxypropyl, hydroxybutyl, methyl, ethyl, propyl, dihydroxypropyl, carboxymethyl, sulfoethyl, hydrophobic long-chain branched and unbranched alkyl groups, hydrophobic long-chain branched and unbranched alkyl aryl groups or aryl alkyl groups, cationic groups, acetate, propionate, butyrate, lactate, nitrate or sulfate, of which some groups, such as, for example, hydroxyethyl, hydroxypropyl, hydroxybutyl, dihydroxypropyl and lactate, are capable of forming grafts. The substituents of the polysaccharides according to the invention are not limited to these groups. Typical polysaccharide derivatives are guar derivatives, starch derivatives, chitin or chitosan derivatives, and preferably cellulose derivatives, but the polysaccharide derivatives according to the invention are not limited to these.

Examples of cellulose derivatives are hydroxyethyl cellulose (HEC), hydroxypropyl cellulose (HPC), ethyl hydroxyethyl cellulose (EHEC), carboxymethyl cellulose, carboxymethyl hydroxyethyl cellulose (CMHEC), hydroxypropyl hydroxyethyl cellulose (HPHEC), methylcellulose (MC), methyl hydroxypropyl cellulose (MHPC), methyl hydroxyethyl cellulose (MHEC), carboxymethyl cellulose (CMC), hydrophobically modified hydroxyethyl cellulose (hmHEC), hydrophobically modified hydroxypropyl cellulose (hmHPC), hydrophobically modified ethyl hydroxyethyl cellulose (hmEHEC), hydrophobically modified carboxymethyl hydroxyethyl cellulose (hmCMHEC), hydrophobically modified hydroxypropyl hydroxyethyl cellulose (hmHPHEC), hydrophobically modified methylcellulose (hmMC), hydrophobic ally modified methyl hydroxypropyl cellulose (hmMHPC), hydrophobically modified methyl hydroxyethyl cellulose (hmMHEC), hydrophobically modified carboxymethyl methylcellulose (hmCMMC), sulfoethyl cellulose (SEC), hydroxyethyl sulfoethyl cellulose (HESEC), hydroxypropyl sulfoethyl cellulose (HPSEC), methyl hydroxyethyl sulfoethylcellulose (MHESEC), methyl hydroxypropyl sulfoethyl cellulose (MHPSEC), hydroxyethyl hydroxypropyl sulfoethyl cellulose (HEHPSEC), carboxymethyl sulfoethyl cellulose (CMSEC), hydrophobically modified sulfoethyl cellulose (hmSEC), hydrophobically modified hydroxyethyl sulfoethyl cellulose (hmHESEC), hydrophobically modified hydroxypropyl sulfoethyl cellulose (hmHPSEC) or hydrophobically modified hydroxyethyl hydroxypropyl sulfoethyl cellulose (hmHEHPSEC).

Preferred cellulose derivatives are cellulose esters or cellulose ethers. Preferred cellulose ethers are carboxy-$C_1$-$C_3$-alkyl celluloses, such as carboxymethyl celluloses; carboxy-$C_1$-$C_3$-alkyl hydroxy-$C_1$-$C_3$-alkyl celluloses, such as carboxymethyl hydroxyethyl celluloses; $C_1$-$C_3$-alkyl celluloses, such as methylcelluloses; $C_1$-$C_3$-alkyl hydroxy-$C_{1-3}$-alkyl celluloses, such as hydroxyethyl methylcelluloses, hydroxypropyl methylcelluloses or ethyl hydroxyethyl celluloses; hydroxy-$C_{1-3}$-alkyl celluloses, such as hydroxyethyl celluloses or hydroxypropyl celluloses; mixed hydroxy-$C_1$-$C_3$-alkyl celluloses, such as hydroxyethyl hydroxypropyl celluloses, or alkoxy hydroxyethyl hydroxypropyl celluloses, the alkoxy group being straight-chain or branched and containing 2 to 8 carbon atoms. Particularly preferred cellulose derivatives are methylcellulose, methyl hydroxyethyl cellulose, methyl hydroxypropyl cellulose, hydroxypropyl cellulose and carboxymethyl cellulose, particularly in its sodium form. Two or more types of polysaccharide derivatives, preferably cellulose derivatives, more preferably two or more types of cellulose ethers, can be incorporated in combination in the dosage form of the present invention. Particularly, a combination of two different types of hydroxypropyl methylcelluloses or methylcelluloses or a combination of i) a hydroxypropyl methylcellulose or methylcellulose and ii) a carboxymethyl cellulose can be used in combination for preparing the dosage forms of the present invention.

Most preferably, the water-soluble cellulose ether is a methylcellulose with a methyl degree of substitution $DS_{methyl}$ of from 1.2 to 2.2, preferably from 1.5 to 2.0; or a hydroxypropyl methylcellulose with a $DS_{methyl}$ of from 0.9 to 2.2, preferably from 1.1 to 2.0, and an $MS_{hydroxypropyl}$ of from 0.02 to 2.0, preferably from 0.1 to 1.2; or a hydroxyethyl methylcellulose with a $DS_{methyl}$ of from 1.15 to 2.3, preferably from 1.15 to 2.2, and an $MS_{hydroxyethyl}$ of from 0.03 to 1.0, preferably from 0.05 to 0.9; or a hydroxyethyl cellulose with an $MS_{hydroxyethyl}$ of from 1.2 to 3.0, preferably from 1.45 to 2.2. The determination of the ether side groups, i.e. the $DS_{methyl}$, $MS_{hydroxyethyl}$ and $MS_{hydroxypropyl}$ can be effected as described by K. L. Ketterer, W. E. Kester, D. L. Wiederrich, and J. A. Grover, Determination of Alkoxyl Substitution in Cellulose Ethers by Zeisel-Gas Chromatographie, Analytical Chemistry, Vol. 51, No. 13, November 1979, 2172-76.

The viscosities of the water-soluble cellulose ethers can vary over a broad range. In one aspect of the present invention the viscosity of the cellulose ether is more than 150 mPa·s, preferably from 500 to 200,000 mPa·s, more preferably from 500 to 100,000 mPa·s, most preferably from 1000 to 80,000, particularly from 1000 to 60,000, determined in a 1.5% by weight aqueous solution at 20° C. in a Haake RS600 rheometer with a cone and plate Geometry)(CP-60/2° at 20° C. and at a shear rate of 2.55 s$^{-1}$. In another aspect of the present invention the viscosity of the cellulose ether is from 1.2 to 200 mPa·s, preferably from 2 to 100 mPa·s, more preferably from 2.5 to 50 mPa·s, in particular from 3 to 30 mPa·s, measured as a 2 weight-% aqueous solution at 20° C. according to ASTM D2363-79 (Reapproved 2006). Such low viscosity cellulose ethers can be produced in a known manner by partial degradation of higher viscosity cellulose ethers.

The production of polysaccharide derivatives, preferably polysaccharide ethers and polysaccharide esters is known in the art. Typically the production process involves activating the polysaccharide, such as cellulose, for example by treatment with an alkali metal hydroxide, reacting the thus treated polysaccharide with a derivatizing agent, such as an etherifying or esterifying agent, and washing the polysaccharide derivative to remove by-products. After the washing step the polysaccharide derivative generally has a moisture content of from 30 to 60 percent, typically from 45 to 55 percent, based on the total weight of the moist polysaccharide derivative. While the preferred washing liquor may depend on the specific type of polysaccharide derivative, preferred washing liquors generally are water, isopropanol, acetone, methylethylketone or brine. More preferred washing liquors generally are water or brine. Cellulose derivatives are generally washed at a temperature of from 20 to 120° C., preferably from 65 to 95° C. A solvent-moist, preferably a water-moist filter cake is obtained after washing and separating the polysaccharide derivative from the washing liquor. The moist polysaccharide derivative is usually obtained in the shape of moist granules, moist lumps and/or a moist paste. The moist polysaccharide derivative can be directly subjected to a drying-grinding step as described below or, e.g., for logistics reasons, can be subjected to an intermediate drying step.

Drying-grinding is generally described in the art as drying and grinding simultaneously in one process step with one unit operation, typically an impact mill or an air swept impact mill Drying is typically accomplished with a combination of hot gas and mechanical energy. Hot air is most commonly used but also hot nitrogen gas can be used. The hot gas and the wet product stream are generally fed via separate inlets into the mill, typically hot gas from the bottom and wet product at a side entrance via a feed screw system connected to the mill Superheated vapor of a solvent, such as superheated steam, or a steam/inert gas mixture or a steam/air mixture can also be used as heat-transfer gas and transport gas, as described in more detail in European Patent Applications EP 0 954 536 A1 (equivalent to U.S. Pat. No. 6,320,043) and EP 1 127 910 A1 (equivalent to U.S. Pat. No. 7,259,257). Preferably the moist polysaccharide derivative is subjected to drying-grinding in a gas-swept impact mill, preferably an air-swept impact mill, wherein the polysaccharide derivative is subjected to an impacting and/or shearing stress. Preferred gas-swept impact mills are Ultra Rotor mills (Altenburger Maschinen Jaeckering, Germany) or Turbofiner PLM mills (PALLMANN Maschinenfabrik GmbH & Co. KG, Germany). Gas classifier mills are also useful gas-swept impact mills, for example, the Hosokawa Alpine Air Classifier mill—ZPS Circoplex Hosokawa Micron Ltd., Cheshire, England. When drying-grinding a moist polysaccharide derivative, the median particle diameter and the bulk density of the polysaccharide derivative can be controlled by controlling the temperature of the polysaccharide derivative prior to drying-grinding, as described in patent application PCT/US10/043,522, filed 28 Jul. 2010. The temperature of the polysaccharide derivative prior to drying-grinding is preferably controlled and optionally varied or adjusted in a range from 5 to 70° C., more preferably from 6 to 65° C., most preferably from 6 to 60° C. If a liquid such as water is added to the polysaccharide derivative prior to drying-grinding, the temperature of the polysaccharide derivative prior to drying-grinding is preferably controlled and optionally varied or adjusted by controlling and optionally varying or adjusting the temperature of the added liquid and/or the jacket temperature of the compounder. This can also be achieved without interrupting the drying-grinding process. The moisture content of the polysaccharide derivative prior to drying-grinding is preferably 40 percent or more, more preferably 45 percent or more, and most preferably 50 percent or more prior to drying-grinding, based on the total weight of the moist polysaccharide derivative. The moisture content is preferably 90 percent or less, more preferably 85 percent or less, and most preferably 82 percent or less prior to drying-grinding, based on the total weight of the moist polysaccharide derivative. The moisture content can be determined by ASTM method D-2363-79 (reapproved 1989). Moreover, if desired in a specific process, wherein the drying-grinding is conducted in a rotational drying-grinding device, the median diameter, the median length and the bulk density of the particles after drying-grinding can be controlled and optionally varied or adjusted by controlling and optionally varying or adjusting the circumferential speed of the drying-grinding device, in addition to controlling the temperature of the polysaccharide derivative prior to drying-grinding. The circumferential speed of the drying-grinding device is preferably controlled and optionally varied or adjusted in a range from 55 to 140 m/s, more preferably from 70 to 120 m/s, most preferably from 90 to 115 m/s.

The polysaccharide derivative is useful as an excipient for a dosage form, particularly as an excipient for a sustained-release dosage form, which means that it has the function to regulate the release of an active ingredient from the dosage form over an extended period of time. The term "sustained-release" is used herein synonymously to the terms prolonged release; extended release; sustained release; depot release; time release; controlled release; modified release or prolonged action. "Sustained release" is an approach by which active compounds, such as biologically active compounds, are made available at a rate and duration designed to accomplish an intended effect. For example, an oral controlled release drug delivery system is a device or dosage form that regulates the release of a drug into the gastrointestinal tract, thereby controlling the absorption rate of that drug in order to achieve a desired blood plasma profile. These dosage forms are designed to provide a constant or nearly constant drug level in plasma with reduced fluctuation via a slow, continuous release of drug over an extended period of time. In the sustained-release dosage form of the present invention it generally takes between 0.75 and 36 hours, more preferably between 4 and 30 hours, and most preferably between 8 and 24 hours to release the active ingredient from the dosage form in its entirety.

The above-described polysaccharide derivatives are useful as an excipient for dosage forms, particularly for sustained-release dosage forms in a variety of technological fields, for example in personal care, laundry care or agricultural applications, water treatment, and particularly in human or animal health care applications, most specifically pharmaceutical applications wherein a biologically active ingredient is selected from vitamins, herbal and mineral supplements and drug substances.

The above-described polysaccharide derivatives have a unique combination of features which makes them very useful as an excipient in dosage forms, for example in pharmaceutical dosage forms. The polysaccharide derivatives have good flow properties. They can be efficiently blended with a biologically active ingredient, and, if desired, with one or more optional adjuvants, even in the absence of a substantial amount of added solvent or heat. It is to be understood that one or more types of the above-described polysaccharide derivatives and one or more types of active ingredients can be blended with one or more optional adjuvants to prepare a dosage form. Preferably the blending process is conducted at about room temperature.

A large variety of active ingredients are useful, dependent on the intended end-use of the dosage form. Active ingredients are known in the art and include, among others, detergents or surfactants for laundry care applications; fertilizers, herbicides or pesticides in formulations designed to release the bioactive agents over a prolonged period of time in agricultural applications. A wide range of biologically active ingredients are useful, such as vitamins, herbals and mineral supplements and drugs. The biologically active ingredient includes hydrophobic, hydrophilic and amphiphilic compounds. The biologically active ingredient may be used for treating indications such as, by way of example and without limitation, inflammation, gout, hypercholesterolemia, microbial infection, AIDS, tuberculosis, fungal infection, amoebic infection, parasitic infection, cancer, organ rejection, diabetes, heart failure, arthritis, asthma, pain, congestion, urinary tract infections, vaginal infection, seizure-related disorders, depression, psychosis, convulsion, diabetes, blood coagulation, hypertension and birth control. The amount of the biologically active ingredient loaded into a pharmaceutical dosage form will vary according to the pharmacological activity of the compound, the indication being treated, the targeted dosing regimen, the projected method of administration, the integrity or stability of the final composition or other such reasons.

The amount of the active ingredient generally is at least 0.5 percent, preferably at least 1 percent, more preferably at least 5 percent, most preferably at least 10 percent, based on the total weight of the dosage form, and generally up to 75 percent, preferably up to 65 percent, more preferably up to 55 percent, most preferably up to 45 percent, based on the total weight of the dosage form. The active ingredient is generally solid and preferably has a median particle diameter as defined further above of from 1 to 500 micrometers. Useful optional adjuvants are known in the art and are generally solid, such as one or more fillers, pigments, colorants, flavorants, disintegrating agents, binders, plasticizers, salts, acidic and basic pH modifiers, antioxidants and/or lubricants. Examples of such adjuvants are acacia, corn starch, guar gum, potato starch, alginic acid, stearic acid, magnesium stearate, lactose, sucrose, dicalcium phosphate, microcrystalline cellulose, sugars, minerals, cellulose powder or cellulose fibers. Optional adjuvants are generally solid and preferably have a median particle diameter as defined further above of from 1 to 500 micrometers.

The blend of one or more types of polysaccharide derivatives, one or more active ingredients and one or more optional adjuvants has good flow properties and exhibits a minimum of segregation which means that the blend shows excellent uniformity. By this it is meant that if the blend is divided into portions, the content of the active ingredient is essentially the same in all portions. The blend can be directly filled into capsules or can be subjected to a direct compression process to produce tablets or similar dosage forms. The efficient feeding of the blend to a capsule filling device or to a compression device allows for uniform weights of the dosage forms. The combination of good powder flow and high bulk density, generally minimum segregation and good compactibility allows the blend to be efficiently processed to a dosage form in a direct compression process, even in the absence of a substantial amount of added solvent, heat, pressure or additional processing steps. By the term "in the absence of a substantial amount of added solvent or heat" is meant that solvent or heat is not added in a sufficient amount to the blend of the active ingredient and the polysaccharide derivative to effect granulation of the blend. Preferably the direct compression process is conducted in the absence of any amount of added solvent or heat.

Direct compression processes to produce tablets are known in the art. Typically a compaction pressure of from 150 MPa to 375 MPa, preferably from 200 to 300 MPa is sufficient to produce tablets of good quality. The direct compression process of the present invention eliminates the need for formulators of dosage forms to subject the blend of one or more polysaccharide derivatives, one or more active ingredients and one or more optional adjuvants to a wet granulation step before compressing the blend to a tablet. A wet granulation step involves wetting, drying and screening steps, which is not desirable for moisture-sensitive or heat-sensitive drugs. The direct compression process of the present invention also eliminates the need for a complicated dry-granulation process. In addition, products made by the direct compression process are less costly than those produced when wet or dry granulation processes are employed.

It has surprisingly been found that sustained release pharmaceutical dosage forms with excellent drug release profiles can be produced when using the polysaccharide derivatives of the present invention, which have a better flowability than the cellulose ethers recommended for sustained release pharmaceutical dosage forms in U.S. Pat. No. 4,734,285 and which have an improved flowability and/or an increased bulk density, as compared to the cellulose ethers disclosed in WO 2008/127794.

The polysaccharide derivatives of the present invention can form at least a portion of a coating, particularly a compression coating, of a dosage form to control the release of the active ingredient. However, more preferably the granular material forms at least a portion of the matrix of a dosage form.

The open-ended terms "comprising," and "comprises," are synonymous with "including," "having," and "characterized by". When referring to a preceding list of elements or steps (e.g., ingredients), the phrases "combination thereof," "mixture thereof," and the like mean any two or more (at least two) up to and including all of the listed elements or steps. The term "optionally" means "with or without" (e.g., "optionally, an additive" means with or without an additive).

EXAMPLES

The following examples are for illustrative purposes only and are not intended to limit the scope of the present invention. Unless otherwise mentioned, all parts and percentages are by weight. Viscosities of the cellulose ethers are measured as a 2 weight percent aqueous solution using a Brookfield LVT viscosimeter at 20° C.

Examples 1-17

The following cellulose ethers listed in Table 1 below are used in the Examples:

K15MFG: A Food Grade hydroxypropyl methylcellulose commercially available from The Dow Chemical Company as METHOCEL™ K15MFG cellulose ether.

K4MFG: A Food Grade hydroxypropyl methylcellulose commercially available from The Dow Chemical Company as METHOCEL™ K4MFG cellulose ether.

K100M: Hydroxypropyl methylcellulose commercially available from The Dow Chemical Company as METHOCEL™ K100M cellulose ether.

E15LV: Hydroxypropyl methylcellulose commercially available from The Dow

Chemical Company as METHOCEL™ E15LV cellulose ether.

K100M DOM: Hydroxypropyl methylcellulose which is produced in the same manner and has the same degree of substitution as the commercially available METHOCEL™ K100M cellulose ether, except that K100M DOM is a material that has not been ground after production but is a dryer outlet material that is directly used in Examples 15-17 for producing the cellulose ether of the present invention.

Percent methoxyl and hydroxypropyl substitution and viscosities of the Cellulose ethers are summarized below.

| Commercial Name | % Methoxyl | % Hydroxypropyl | Viscosity (mPas) |
|---|---|---|---|
| METHOCEL K100M Premium CR | 22.0-24.0 | 9.5-11.5 | 75,000-140,000 |
| METHOCEL K100M Premium DC | 22.0-24.0 | 9.5-11.5 | 75,000-140,000 |
| METHOCEL K15M Food Grade | 19.0-24.0 | 7.0-12.0 | 11,250-21,000 |
| METHOCEL K4M Food Grade | 19.0-24.0 | 7.0-12.0 | 3,000-5,600 |
| METHOCEL E15 Food Grade | 28.0-30.0 | 7.0-12.0 | 12-18 |

CRT20000PA: Sodium carboxymethyl cellulose powder having a degree of DS(carboxymethyl) of 0.65-0.95 and a viscosity of about 20000 mPa·s. The sodium carboxymethyl cellulose powder is commercially available from Dow Wolff Cellulosics (a subsidiary of The Dow Chemical Company) as Walocel™ C CRT20000PA.

A commercially available continuous compounder with heating and cooling jacket is used to add water to dry cellulose ether. The compounder jacket is supplied with a fluid of −10° C. to 70° C. Cellulose ether at a moisture level of less than 5% is fed continuously at a feed rate of 10-30 kg/h into the compounder. Water of a temperature of 5° C. to 20° C. is continuously added at rates of 1-120 kg/h to the compounder resulting in a moisture level of about 50-82%. The more specific reaction conditions are listed in Table 1 below. The wet product is transported continuously via a transport belt into a mill feed unit (Altenburger Maschinen Jaeckering GmbH, Hamm, Germany). The bottom blades of the vessel agitator press the paste into a single augur screw mounted at the bottom of the vessel. The wet product is forced through a perforated plate directly into the side of an Ultrarotor II "S" impact mill (Altenburger Maschinen Jaeckering GmbH, Hamm, Germany) between the first and second grinding stage. The mill is equipped with seven grinding stages. The bottom three grinding stages are equipped with standard grinding bars. Turbo-bars are installed in the top four grinding stages. A co-rotating finger sifter wheel with twelve blades is installed on the top of the 7th grinding stage. The interior of mill jacket has the standard Altenburger corrugated stationary grinding plates.

The rotor of the impact mill is operated at a circumferential speed of 91 or 114 m/s. A hot nitrogen stream is fed at a rate listed in Table 1 below into the bottom of the mill A cyclone is used to separate the dried product from the nitrogen. The final product moisture is smaller than 3% by weight.

Comparative Example A (CR)

Hydroxypropyl methylcellulose ether having a degree of substitution of methoxyl groups of 22.6% and of hydroxypropoxyl groups of 10.3%, and a viscosity of 114,700 Pa·s, is used as a comparative material. It is representative of state of the art controlled release grade cellulose ether and referred to as CR cellulose ether. The production of controlled release grade cellulose ethers is disclosed in U.S. Pat. No. 4,734,285.

Comparative Example B (DC)

Hydroxypropl methylcellulose ether having a degree of substitution of methoxyl groups of 22.7% and of hydroxypropoxyl groups of 10.0%, and a viscosity of 103,300 mPa·s, is used as a comparative material. The hydroxypropyl methylcellulose of Comparative Example B can be produced by a granulation process as described in WO 2008/127794. The hydroxypropyl methylcellulose of Comparative Example B is referred to as "Direct Compression" (DC) cellulose ether.

TABLE 1

| (Comparative) Example | Cellulose Ether (CE) A | Cellulose Ether (CE) B | Wt. % A/B | Brookfield Viscosity [mPa·s] | Moisture Wet CE [%] | Water Temperature [° C.] | Temperature of wet CE [° C.] | Nitrogen Flow Mill [m3/hr] | Mill Blade Tip Speed [m/s] |
|---|---|---|---|---|---|---|---|---|---|
| 1 | K15MFG | E15LV | 25/75 | 99.0 | 65 | 19 | 61 | 715 | 114 |
| 2 | K15MFG | E15LV | 25/75 | 202.0 | 50 | 19 | 60 | 1376 | 114 |
| 3 | K15MFG | E15LV | 25/75 | 104.0 | 65 | 16 | 21 | 667 | 114 |
| 4 | K15MFG | E15LV | 25/75 | 182.0 | 59 | 14 | 40 | 1071 | 114 |
| 5 | K15MFG | E15LV | 25/75 | 116.0 | 51 | 20 | 61 | 561 | 114 |
| 6 | K15MFG | E15LV | 25/75 | 129.0 | 58 | 20 | 42 | 896 | 114 |
| 7 | K15MFG | E15LV | 25/75 | 179.0 | 66 | 13 | 19 | 1415 | 114 |
| 8 | K4MFG | CRT20000PA | 20/80 | *) | 71 | 5 | 30 | 1002 | 114 |
| 9 | K4MFG | CRT20000PA | 50/50 | *) | 59 | 5 | 40 | 1069 | 114 |
| 10 | K4MFG | CRT20000PA | 50/50 | *) | 59 | 5 | 40 | 991 | 114 |
| 11 | K4MFG | CRT20000PA | 80/20 | *) | 68 | 5 | 59 | 979 | 114 |
| 12 | K4MFG | CRT20000PA | 20/80 | *) | 67 | 5 | 61 | 936 | 114 |
| 13 | K100M | — | 100 | 89200 | 67 | 5 | 22 | 1900 | 114 |
| 14 | K100M | — | 100 | 91400 | 76 | 7 | 19 | 1030 | 91 |
| 15 | K100M_DOM | — | 100 | 147600 | 65 | 6 | 40 | 1051 | 114 |
| 16 | K100M_DOM | — | 100 | 151500 | 80 | 11 | 40 | 987 | 114 |
| 17 | K100M_DOM | — | 100 | 133900 | 80 | 11 | 20 | 565 | 114 |
| A (CR) | K100M CR | — | 100 | 114,700 | — | — | — | — | — |
| B (DC) | K100M DC | — | 100 | 103,300 | — | — | — | — | — |

*) not measured

The DIFI, Equivalent Projected Circle Diameter (EQPC), length (LEFI), elongation, aspect ratio and sphericity of the particles in the powder samples of Examples 1-17 and Comparative Examples A and B are measured or calculated with a high speed image analyzer (high speed image analyzer sensor QICPIC, Sympatec, Germany, with dry disperser RODOS/L with an inner diameter of 4 mm and dry feeder VIBRI/L and divide Software WINDOX5, Vers. 5.3.0 and M7 lens). The volume percentages of fine particles, fibrous particles, and other (spherical) particles are calculated from these parameters as described further above and listed in Table 2 below. The median EQPC (50% of the EQPC of the particle distribution is smaller than the given value in µm and 50% is larger, as calculated from the volume distribution) and the median LEFI (50% of the LEFI of the particle distribution is smaller than the given value in µm and 50% is larger, as calculated from the volume distribution) are also listed in Table 2 below.

Particle flowability is measured by a flow test method. The apparatus for the flow test method consists of two Plexiglass pieces, specifically a cylindrical part (column) which is 305 mm tall with an inner diameter of 89 mm; and a conical part (a vertex down cone) with a height of 108 mm, a top diameter of 89 mm and an outlet diameter (orifice) of 51 mm. The vertex angle φ of the cone is 39.2°. By all diameters the inner diameters are meant, excluding the wall thickness. A schematic illustration of the apparatus for the flow test method is illustrated in FIG. 1. The vertex angle φ of the right circular vertically inverted cone (i.e. vertex down cone) is the angle made by a cross section through the vertex and the center of the base. The total volume of the tester is 2.32 liters. The two pieces are connected. The tester is set up vertically with the vertex of the cone at the bottom. The particle flow rate is measured by first blocking the outlet of the cone with a plate, and then filling the tester completely with non-compacted polysaccharide derivative in particulate form by pouring the polysaccharide derivative into the top of the cylinder and filling the cylinder completely. The polysaccharide derivative is discharged from the hopper into a collection container by removing the plate. A timer is used to record the total time for the particles to discharge from the hopper. The polysaccharide derivative in the collection container is then weighed and the time and weight are recorded. The flowability, also designated as flow rate, is calculated as the ratio of the weight of polysaccharide derivative per unit time. Each material is tested four times and the average flow rate is recorded.

The untapped bulk density of the polysaccharide derivative in particulate form is measured using a Hosokawa Powder Characteristics Tester: Model PT-N available from Hosokawa Micron, Osaka Japan.

TABLE 3

| Ingredients | Manufacturer | Wt % |
|---|---|---|
| hydroxypropyl methylcellulose | The Dow Chemical Company, USA | 30 |
| Ketoprofen | Spectrum Chemicals, USA | 20 |
| Impalpable Lactose | Sheffield, USA | 49 |
| Magnesium Stearate | Mallinckrodt, USA | 1 |

Tablets are allowed to relax for 24 hours before testing. Each tablet is weighted using an analytical balance and then each tablet is crushed using a HT-300 Hardness tester. The sustained release performance of the tablets is also compared. The release of ketoprofen is measured using 6 tablets from each formulation. Drug release is measured using a commercially available Varian Total Solution with Dual VK 7025 dissolution system. A USP Type II dissolution apparatus is used to determine drug release performance. The paddle stirring rate is set to 50 RPM and the dissolution media, maintained at 37° C., is 0.05M phosphate buffer at a pH of 5.8. Detection of dissolved ketoprofen is achieved using ultraviolet absorption spectrometry at a wavelength of 260 nm.

Figure 2:
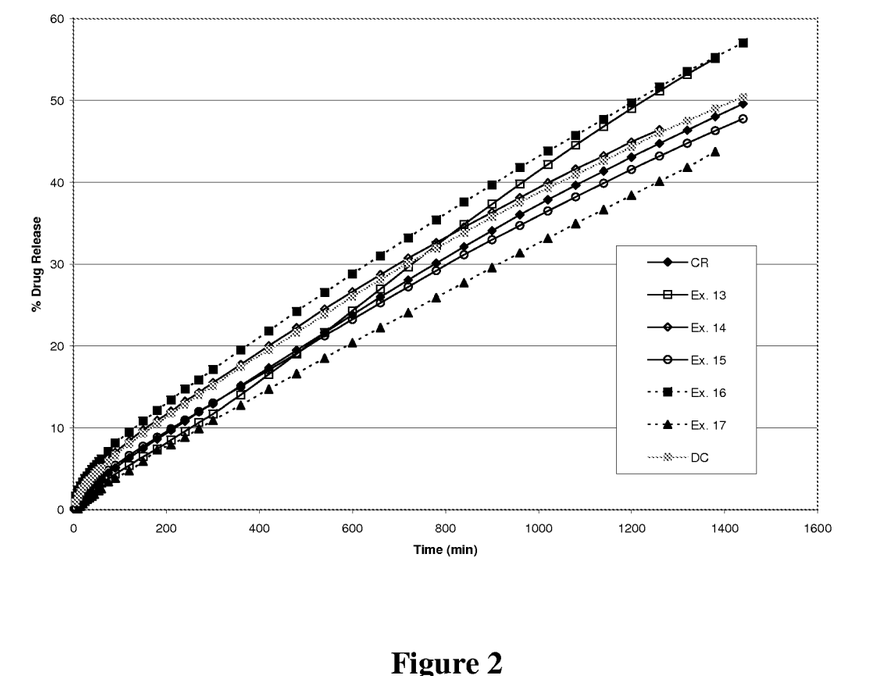
FIG. 2 illustrates the controlled release of a first drug from pharmaceutical dosage forms of the present invention and pharmaceutical dosages forms known from U.S. Pat. No. 4,734,285 and WO/2008/127794.

As shown in FIG. 2, the drug release profiles of ketoprofen from tablets produced from compositions comprising the

TABLE 2

| (Comparative) Example | Median LEFI [microns] | Median EQPC [microns] | Bulk Density [kg/m³] | Flowability [g/s] | Fine particles [% volume] | Fibrous particles [% volume] | Other (spherical) particles [% volume] |
|---|---|---|---|---|---|---|---|
| 1 | 77.8 | 58.86 | 337 | 106 | 12.8 | 1.9 | 85.3 |
| 2 | 123.34 | 72.13 | 312 | 56 | 7.4 | 8.4 | 84.2 |
| 3 | 93.88 | 65.11 | 399 | 66 | 9.1 | 3.8 | 87.1 |
| 4 | 103.25 | 68.1 | 330 | 72 | 7.6 | 4.9 | 87.5 |
| 5 | 66.0 | 48.2 | 375 | 76.8 | 28.1 | 2.3 | 69.6 |
| 6 | 84.23 | 62.94 | 351 | 77 | 7.3 | 2.4 | 90.4 |
| 7 | 178.34 | 95.07 | 399 | 84 | 3.4 | 13.5 | 83.2 |
| 8 | 87.6 | 54.3 | 503 | 73.5 | 16.0 | 6.0 | 78.0 |
| 9 | 122.6 | 58.1 | 413 | 68.9 | 14.0 | 12.0 | 74.0 |
| 10 | 129.2 | 59.5 | 416 | 72.0 | 13.0 | 13.0 | 74.0 |
| 11 | 141.7 | 64.2 | 373 | 60.4 | 11.0 | 13.0 | 76.0 |
| 12 | 100.6 | 52.9 | 478 | 59.3 | 20.0 | 8.0 | 72.0 |
| 13 | 253.7 | 119.3 | 276 | 80.8 | 2.5 | 28.4 | 69.1 |
| 14 | 165.0 | 88.8 | 327 | 86.0 | 4.2 | 14.1 | 81.7 |
| 15 | 266.9 | 75.9 | 377 | 64.3 | 5.4 | 19.2 | 75.4 |
| 16 | 151.0 | 60.5 | 441 | 60.3 | 12.6 | 5.5 | 81.9 |
| 17 | 82.5 | 51.7 | 495 | 85.9 | 23.2 | 2.2 | 74.6 |
| A (CR) | 264.6 | 93.3 | 302 | 31.9 | 4.9 | 41.1 | 54.0 |
| B (DC) | 395.3 | 152.5 | 164 | 43 | 2.5 | 46.4 | 51.2 |

Table 2 illustrates the improved flowability, and in the preferred embodiments of the present invention also the higher bulk density, of the polysaccharide derivatives of the present invention, as compared to the known polysaccharide derivatives of comparative Examples A and B.

Dosage Forms Produced from Ketoprofen Compositions Comprising the Hydroxypropyl Methylcellulose of Examples 13, 14, 15, 16, or 17 or Comparative Example A or B The controlled drug release performance using a Ketoprofen dosage form is determined after 3 and 12 hours. Ketoprofen, hydroxypropyl methylcellulose, and impalpable lactose as listed in Table 3 are blended in a Turbula jar blender for 10 minutes. Magnesium stearate is added and the pharmaceutical composition blended for an additional 1 minute. The resulting formulated system is fed into a Manesty BETA tablet press with a target tablet weight of 400 mg. The tooling used in the press is 10.3 mm in diameter round, flat-faced and bevel-edged. The tablet press is set at a speed of 12-14 RPM (revolutions per minute) and the tablets are compressed at a target compression force of 5000 lbs (22.2 kN), producing a compaction pressure of 266 MPa.

novel cellulose ethers of Examples 13, 14, 15, 16, and 17 as excipients show similar drug release as tablets produced from compositions comprising the CR grade or DC grade cellulose ethers of Comparative Examples A and B.

Dosage Forms Produced from Metoprolol Tartrate Compositions Comprising the Hydroxypropyl Methylcellulose of Examples 13, 14 or 15 or Comparative Examples A or B Metoprolol tartrate, microcrystalline cellulose and Starch 1500® are blended as listed in Table 4 below in a V-blender for 10 minutes to prepare a pharmaceutical formulation. Magnesium stearate is added and the pharmaceutical composition is blended for an additional 1 minute.

TABLE 4

| Ingredients | Manufacturer | Wt % |
|---|---|---|
| hydroxypropyl methylcellulose | The Dow Chemical Company, USA | 30 |
| Metoprolol Tartrate (active ingredient) | Mulji Mehta & Sons, Private Ltd, India | 10 |

TABLE 4-continued

| Ingredients | Manufacturer | Wt % |
|---|---|---|
| Avicel Microcrystalline Cellulose (PH 102) | FMC Biopolymers, USA | 49.5 |
| Starch 1500 ® | Colorcon, USA | 10 |
| Magnesium Stearate | Mallinckrodt, USA | 0.5 |

The metoprolol tartrate compositions are compressed into tablets according to a direct compression process. The tablets are made using a Manesty BETA tablet press with a target tablet weight of 400 mg. The tooling used in the press is 10.3 mm in diameter round, flat-faced and bevel-edged. The tablet press is set at a speed of about 17 RPM (revolutions per minute) and the tablets are compressed at a target compression force of 5000 lbs (22.2 kN), producing a compaction pressure of 266 MPa. The formulations are tableted with each run lasting about 45 minutes. Tablets are allowed to relax for 24 hours before testing. Each tablet is weighted using an analytical balance and then each tablet is crushed using a HT-300 Hardness tester.

Table 5 below illustrates the comparison of properties of tablets produced from compositions comprising cellulose ethers listed in Table 5 below. Metoprolol tartrate formulations made using cellulose ethers of the present invention achieve the target tablet weight and show less tablet to tablet weight variability than those made from the formulations made using CR or DC grade cellulose ethers of Comparative Examples A or B. Achieving the target tablet weight and less tablet to tablet variability is an indication of the superior bulk density and flow properties of the cellulose ethers of the present invention. Moreover, tablets produced from formulations comprising cellulose ethers of the present invention also have a significantly higher average tablet weight when compared to tablets produced from formulations comprising cellulose ethers of Comparative Example B.

TABLE 5

| Cellulose Ether | Average Tablet Weight (mg) | Standard Deviation | Hardness (SCU) | Standard Deviation |
|---|---|---|---|---|
| Comp. Ex. A (CR) | 409.5 | 12.82 | 22.6 | 1.67 |
| Comp. Ex. B (DC) | 374.7 | 5.23 | 19.0 | 0.73 |
| Ex. 13 | 411.8 | 3.70 | 21.6 | 1.10 |
| Ex. 14 | 412.3 | 4.17 | 18.9 | 0.77 |
| Ex. 15 | 418.6 | 5.11 | 19.3 | 0.74 |

Table 5 also shows a comparison of tablet average hardness values for the metoprolol tartrate formulations. Tablets produced from formulations comprising cellulose ethers of the present invention show less variability in tablet to tablet hardness than tablets produced from formulations comprising known cellulose ethers of Comparative Example A.

Figure 3:
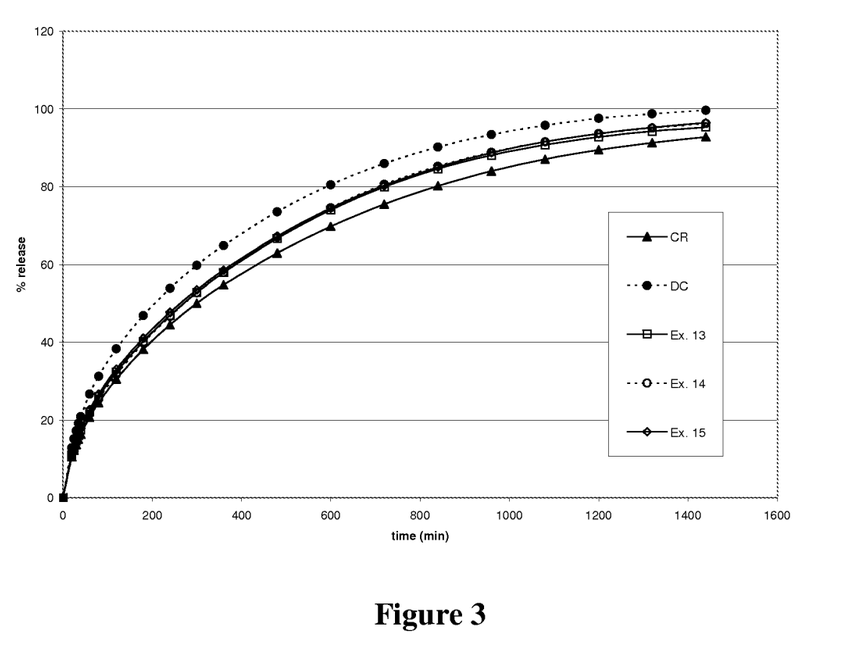
FIG. 3 illustrates the controlled release of a second drug from pharmaceutical dosage forms of the present invention and pharmaceutical dosages forms known from U.S. Pat. No. 4,734,285 and WO/2008/127794.

The sustained release performance of the tablets are also compared. The release of metoprolol tartrate is measured using 6 tablets from each formulation. The tablets are dissolved in deionized water at 37° C., USP II Apparatus at 50 rpm, using a commercially available Varian Total Solution with Dual VK 7025 dissolution system. As shown in FIG. 3, the drug release profiles of metoprolol tartrate from tablets produced from compositions comprising the novel cellulose ethers of Examples 13, 14 or 15 as excipients show similar drug release as tablets produced from compositions comprising the known cellulose ethers of Comparative Example A or B.

The invention claimed is:

1. A polysaccharide derivative which is a particulate cellulose ether or cellulose ester having a median Equivalent Projected Circle Diameter (EQPC) of at least 30 micrometers and less than 140 micrometers and a particle size and shape distribution such that
   no more than 40 volume percent of the polysaccharide derivative particles are fine particles having a particle length LEFI of less than 40 micrometers and ii) no more than 40 volume percent of the polysaccharide derivative particles are fibrous particles, and the sum of the fine particles and the fibrous particles does not exceed 50 volume percent.

2. The polysaccharide derivative of claim 1 having a particle size and shape distribution such that non-compacted polysaccharide derivative particles have a flowability of at least 45 g/sec. through a vertically inverted cone having a vertex angle of about 40° and an outlet diameter of about 50 mm.

3. The polysaccharide derivative of claim 1 having a particle size and shape distribution such that i) no more than 30 volume percent of the particles are fine particles having a particle length LEFI of less than 40 micrometers and ii) no more than 30 volume percent of the particles are fibrous particles, and the sum of the fine particles and fibrous particles does not exceed 40 volume percent.

4. The polysaccharide derivative of claim 1 having a median Equivalent Projected Circle Diameter (EQPC) of no more than 130 micrometers.

5. The polysaccharide derivative of claim 1 having an untapped bulk density of more than 0.35 kg/m$^3$.

6. A dosage form produced from
   a) one or more polysaccharide derivatives of claim 1, b) one or more active ingredients, and c) one or more optional adjuvants.

7. The dosage form of claim 6 being a compressed dosage form wherein the polysaccharide derivative forms at least a portion of the matrix of the dosage form.

8. The dosage form of claim 6 wherein the polysaccharide derivative forms at least a portion of the coating of the dosage form.

9. The dosage form of claim 6 being a sustained-release dosage form.

10. A process for preparing a dosage form comprising the step of
   I.) blending one or more polysaccharide derivatives, one or more active ingredients, and one or more optional adjuvants, and
   II.) compressing the blend to a dosage form,
      wherein said one or more polysaccharide derivatives have a median Equivalent Projected Circle Diameter (EQPC) of less than 140 micrometers and a particle size and shape distribution meeting condition A or B or both:
      A. non-compacted polysaccharide derivative particles have a flowability of at least 45 g/sec through a vertically inverted cone having a vertex angle of about 40° and an outlet diameter of about 50 mm, or
      B. i) no more than 40 volume percent of the polysaccharide derivative particles are fine particles having a particle length LEFI of less than 40 micrometers and ii) no more than 40 volume percent of the polysaccharide derivative particles are fibrous particles, and the sum of the fine particles and the fibrous particles does not exceed 50 volume percent.

11. The process of claim 10 wherein in step I.) one or more polysaccharide derivatives, one or more active ingredients, and one or more optional adjuvants are blended in the absence of a substantial amount of added solvent or heat.

12. The polysaccharide derivative of claim 2
    having a particle size and shape distribution such that i) no more than 30 volume percent of the particles are fine particles having a particle length LEFI of less than 40 micrometers and ii) no more than 30 volume percent of the particles are fibrous particles, and the sum of the fine particles and fibrous particles does not exceed 40 volume percent,
    having a median Equivalent Projected Circle Diameter (EQPC) of no more than 130 micrometers, and
    having an untapped bulk density of more than 0.35 kg/m$^3$.

13. The polysaccharide derivative of claim 12 being a cellulose ether or cellulose ester selected from the group consisting of methylcellulose, methyl hydroxyethyl cellulose, methyl hydroxypropyl cellulose, hydroxypropyl cellulose, sodium carboxymethyl cellulose and combinations thereof.

14. The dosage form of claim 6 wherein the polysaccharide derivative has
    a particle size and shape distribution such that i) no more than 30 volume percent of the particles are fine particles having a particle length LEFI of less than 40 micrometers and ii) no more than 30 volume percent of the particles are fibrous particles, and the sum of the fine particles and fibrous particles does not exceed 40 volume percent, and
    a median Equivalent Projected Circle Diameter (EQPC) of no more than 130 micrometers.

15. The polysaccharide derivative of claim 1 being a methyl hydroxypropyl cellulose.

16. The polysaccharide derivative of claim 13 being a methyl hydroxypropyl cellulose.

* * * * *